United States Patent [19]

Osawa

[11] Patent Number: 5,151,628
[45] Date of Patent: Sep. 29, 1992

[54] LIGHT EMITTING DIODE FOR PHOTOSENSOR AND PHOTOSENSOR WITH SUCH A DIODE

[75] Inventor: Masahiko Osawa, Osaka, Japan

[73] Assignee: Sumitomo Electric Industries, Ltd., Osaka, Japan

[21] Appl. No.: 745,152

[22] Filed: Aug. 15, 1991

[30] Foreign Application Priority Data

Aug. 27, 1990 [JP] Japan ............................. 2-89655[U]
Aug. 27, 1990 [JP] Japan ............................. 2-89656[U]

[51] Int. Cl.$^5$ ............................................. H01J 63/04
[52] U.S. Cl. ..................................... 313/499; 313/110; 250/205; 357/19
[58] Field of Search ................ 313/499, 110; 128/663, 128/665, 666, 672, 675; 250/205; 357/19

[56] References Cited

U.S. PATENT DOCUMENTS 5,045,683  9/1991  Kanda ................... 250/205

FOREIGN PATENT DOCUMENTS 60-158803  10/1985  Japan .
2295542    12/1990  Japan .

Primary Examiner—Donald J. Yusko
Assistant Examiner—Diab Hamadi
Attorney, Agent, or Firm—W. G. Fasse

[57] ABSTRACT

A light emitting diode for a photosensor is so constructed that ambient temperature drifts are prevented from adversely affecting a measurment. The light emitting diode for a photosensor has a substrate (12) carrying a light emitting element (LED$_2$) and a light receiving element (PD) for sensing light emitted by the light emitting element (LED$_2$) thereby to detect a change in the amount of light from the light coming emitting element (LED$_2$) in accordance with a change in the ambient temperature. For this purpose a first transparent layer (21) is provided on the substrate (12) to cover the light emitting element and the light receiving element (PD). A second transparent layer (22) is provided on the first transparent layer (21). A very thin air layer is interposed between the first and second transparent layer.

8 Claims, 5 Drawing Sheets

LIGHT EMITTING DIODE FOR PHOTOSENSOR AND PHOTOSENSOR WITH SUCH A DIODE

FIELD OF THE INVENTION

The present invention relates generally to light emitting diodes for photosensors and, more particularly, to an improved light emitting diode for a photosensor which enables correction of changes in the amount of light from a light emitting element in response to changes in the ambient temperature. The invention further relates to a photosensor using such a light emitting diode.

BACKGROUND INFORMATION

Conventionally, an apparatus has been known which transmits light from one side to the other side of a finger tip and detects changes in the transmittance (reflectance) of the transmitted light, for examining the amount of blood flowing in the finger. A resultant detected signal is then processed and the pulse rate, blood pressure and the like are evaluated by calculation. One example of a photosensor for use in such an apparatus is disclosed in Japanese Utility Model Laying-Open No. 60-158803.

Figure 1:
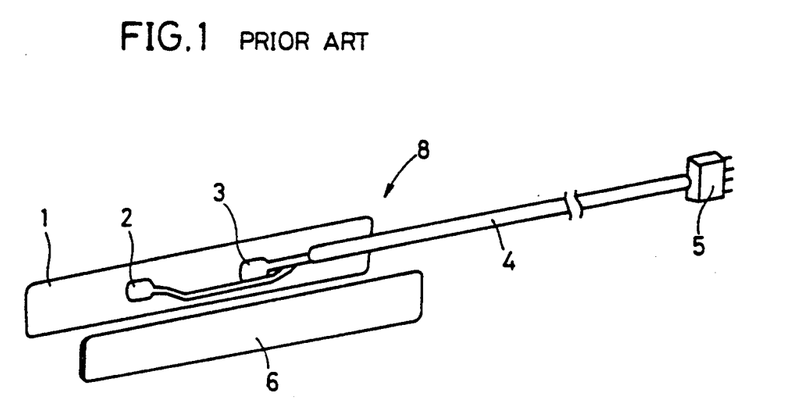
FIG. 1 is a perspective view of a conventional photosensor.
Figure 2:
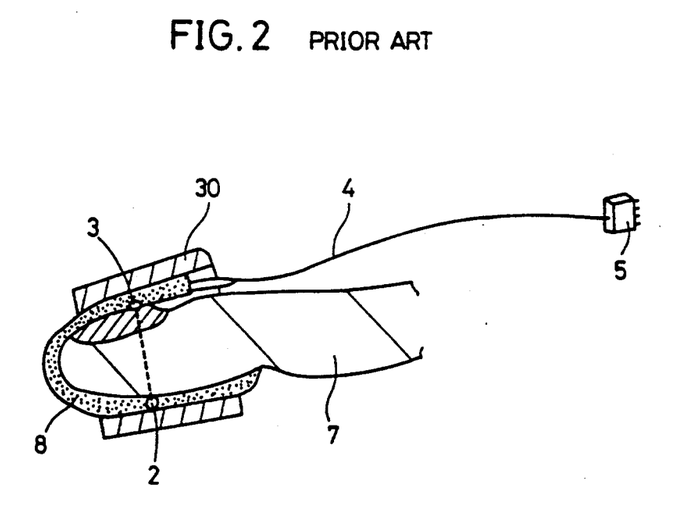
FIG. 2 is a cross-sectional view of the photosensor of FIG. 1 attached to a finger.

FIG. 1 is a perspective view of a conventional photosensor, and FIG. 2 is a cross-sectional view of the photosensor of FIG. 1 attached to a finger.

Referring to FIG. 1, a conventional photosensor 8 transmits light from one side to the other side of a finger for detecting changes in the transmittance of the light. A light emitting element 2 and a light receiving element 3 are disposed with a predetermined spacing therebetween corresponding to the size of the finger, on an easily bendable film substrate 1. A transparent and easily bendable transparent film 6 is placed or attached to film substrate 1 to cover light emitting element 2 and light receiving element 3.

Referring to FIG. 2, the photosensor 8 is used by winding it around a finger 7 to interpose the tip of finger 7 between light emitting element 2 and light receiving element 3. A fixing tape 30 (e.g., a so-called magic tape) is attached around photosensor 8 wound around finger 7. Photosensor 8 is securely fixed on finger 7 by winding fixing tape 30 around photosensor 8 and overlapping the surface of one end of fixing tape 30 and the reverse surface of the other end thereof. When power is supplied from a signal processing unit (not shown) through a connecter 5 to a lead 4, light emitting element 2 emits light. The emitted light is transmitted through finger 7 and directed onto light receiving element 3 which receives light and transmits a resultant signal through lead 4 and connector 5 to the signal processing unit. The signal processing unit detects a change in the transmittance of the light provided at this time, processes a detected signal thereof and then evaluates the pulse rate and blood pressure value by calculation.

In general, a light emitting diode is used as the light emitting element 2 employed in the above-described photosensor 8. The light emitting diode has, however, an undesirable property in that its output power and a wavelength of light emitted from the diode vary depending on the ambient temperatures. If photosensor 8 is attached to a living body, e.g. finger 7, then finger 7 becomes ischemic or hemostatic, resulting in a decrease in the body temperature of finger 7 or in an increase in the body temperature thereof due to an increase in blood pressure. Thus, the ambient temperature of light emitting element 2 varies and its output power and its measured wavelength of light vary accordingly. However, it is desirable that the output power of light emitting element 2 and the wavelength of the light emitted from light emitting element 2 are kept constant in order to accurately measure a pulse rate or a blood pressure value.

Figure 3A:
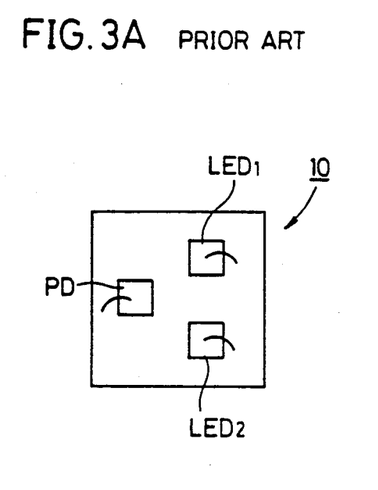
FIG. 3A is a plan view showing one example of a conventional light emitting diode.
Figure 3B:
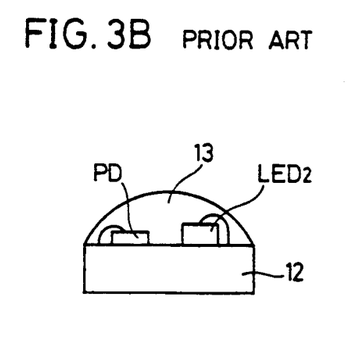
FIG. 3B is a side view of the light emitting diode of FIG. 3A.

In another disclosure a light emitting diode has been proposed which is shown in FIGS. 3A and 3B as the one satisfying the above requirements Japanese Patent Application No. 1-116757 FIG. 3A is a plan view of the kanda light emitting diode, and FIG. 3B is a side view of the diode of FIG. 3A. With reference to FIGS. 3A and 3B, a light emitting diode 10 includes two LED chips $LED_1$ and $LED_2$ disposed on a substrate 12. A photodiode PD is provided in the vicinity of LED chips $LED_1$ and $LED_2$. Photodiode PD directly receives light emitted from chips $LED_1$ and $LED_2$.

Photodiode PD detects a change in the amount of the light emitted from the chips $LED_1$ and $LED_2$ in accordance with a change in the ambient temperatures. A transparent epoxy resin 13 is applied onto substrate 12 to cover the chips $LED_1$ and $LED_2$ and the photodiode PD.

An operation will now be described. Photodiode PD, which is a light receiving element provided separately from the light receiving element of FIG. 1, is disposed near the chips $LED_1$ and $LED_2$. Photodiode PD detects a change in the amount of the light from the light emitting diode in accordance with a change in the ambient temperature. A current flowing through the chips $LED_1$ and $LED_2$ is controlled so as to correct the change in the amount of the light. This feature makes it possible to keep the output power of and the wavelength of the light emitted by the chips $LED_1$ and $LED_2$ constant and thus to obtain an accurate information as to a living body.

The light emitting diode thus structured has, however, room for further improvement.

Figure 4:
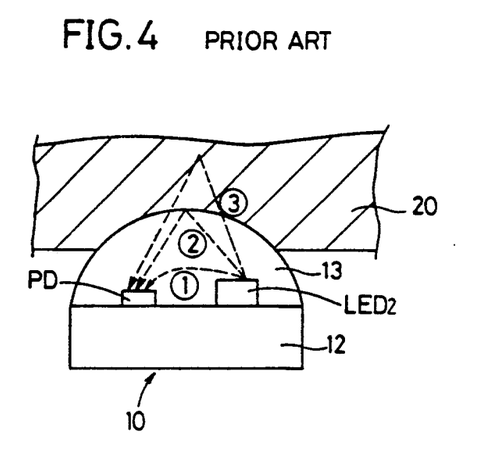
FIG. 4 is a diagram for use in explaining the operation of the conventional light emitting diode.

With reference to FIG. 4, since the light emitting diode 10 is used in contact with a living body 20, there are three types of light beams: a light beam designated by the dotted line ① which is emitted from the chip $LED_2$ and is directly incident on photodiode PD; a light beam designated by the dotted line ② which undergoes a total reflection from an inner surface of epoxy resin 13 and enters into photodiode PD; and a light beam designated by the dotted line ③ which once enters into living body 20 and is then scattered or reflected by living body 20, entering into photodiode PD. The amount of the scattered light or the reflected light denoted by the dotted line ③ is not constant. Accordingly, there occurs an error in a feedback apparatus for monitoring the amount of the light emitted from the chips $LED_1$ and $LED_2$ to maintain a constant light output becomes impossible.

SUMMARY OF THE INVENTION

It is an object of the present invention to provide an improved light emitting diode for a photosensor which is not affected by an influence caused by a drift of ambient temperatures.

Another object of the present invention is to provide an improved light emitting diode for a photosensor which enables the amount of light from a light emitting element to be kept precisely constant.

A further object of the present invention is to provide an improved light emitting diode for a photosensor which enables an accurate monitor of the amount of light from a light emitting element.

A still further object of the present invention is to provide an easily manufacturable light emitting diode for a photosensor.

A still further object of the present invention is to provide a photosensor including an improved light emitting diode which is not influenced by a drift of ambient temperatures.

To accomplish the above objects, a light emitting diode for a photosensor in accordance with the present invention includes a substrate and a light emitting element provided on the substrate. A light receiving element for receiving light emitted by the light emitting element to detect a change in the amount of the light coming from the light emitting element in accordance with a change in the ambient temperature, is disposed on the substrate and in the vicinity of the light emitting element. A first transparent layer is formed on the substrate to cover the light emitting element and the light receiving element. A second transparent layer is formed on the first transparent layer.

Preferably, at least one of the first and second transparent layers is formed of a material which intercepts light other than the wavelengths of a spectrum emitted by the light emitting element.

Preferably, an interface between the first and second transparent layers is hemispherical.

A light emitting diode for a photosensor according to another aspect of the present invention includes a substrate and a light emitting element provided on the substrate. A light receiving element which receives light emitted by the light emitting element to detect a change in the amount of the light coming from the light emitting element in accordance with a change in the ambient temperatures, is disposed on the substrate and near the light emitting element. A first transparent layer is formed on the substrate to cover the light emitting element and the light receiving element. A second transparent layer is formed on the first transparent layer. A refractive index $n_1$ of the first transparent layer and a refractive index $n_2$ of the second transparent layer satisfy the following inequality: $n_1 \geq n_2$.

A photosensor according to still another aspect of the present invention includes a light emitting diode of the present invention having the foregoing characteristics.

In accordance with a light emitting diode for a photosensor according to the present invention, a second transparent layer is formed on a first transparent layer. Thus, a very thin air layer is enclosed between the first and second transparent layers when the second transparent layer is applied over the first transparent layer. The refractive index of air is smaller than those of the first and second transparent layers, whereby the number of optical paths of the light, which is emitted by the light emitting element increases and the emitted light is subjected to a total reflection by an inner surface of the first transparent layer whereby the reflected light incident on the light receiving element also increases. This feature makes it possible to substantially neglect the amount of the light which enters in a living body and then is reflected therefrom. Consequently, the amount of the light emitted by the light emitting element, which is directly received by the light receiving element, increases. When the refractive index $n_1$ of the first transparent layer is larger than the refractive index $n_2$ of the second transparent layer, the number of optical paths of the light emitted by the light emitting element increases, whereby the emitted light undergoes a total reflection at the interface between the first and second transparent layers and the reflected light entering into the light receiving element also increases. This makes it possible to substantially neglect the amount of the light which enters into and then reflects from the living body. Consequently, the amount of the light emitted from the light emitting element, which is directly received by the light receiving element increases.

A photosensor including a light emitting diode of the invention having the foregoing characteristics, permits a precise measurement immune to since it is not influenced by a drift of temperature.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 5:
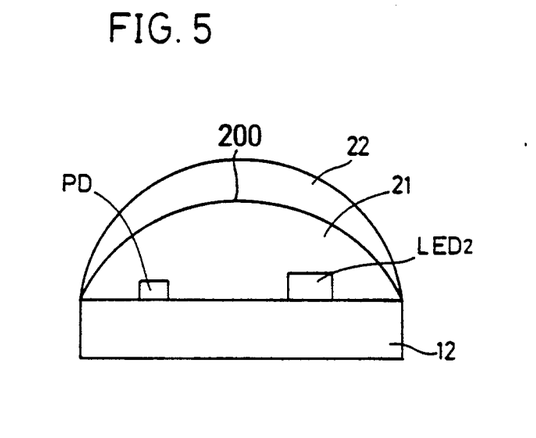
FIG. 5 is a side view of a light emitting diode for a photosensor according to a first embodiment of the present invention.
Figure 7:
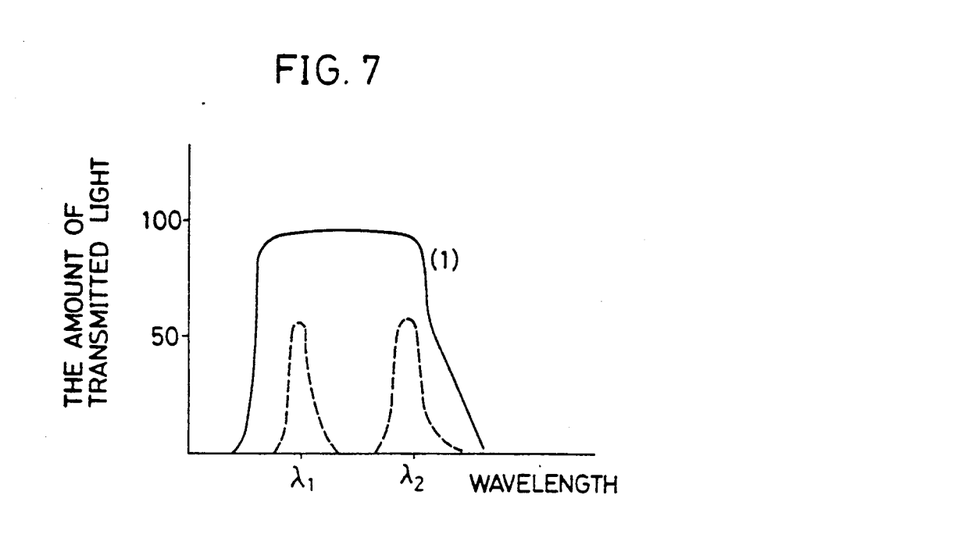
FIG. 7 is a diagram showing a transparence property of an epoxy resin of the type which limits a wavelength band, used in the present invention.

FIG. 5 is a side view of a light emitting diode for a photosensor according to the first embodiment of the present invention. The light emitting diode for a photosensor includes a substrate 12. LED chips LED$_1$ (not shown) and LED$_2$ serving as light emitting elements are disposed on substrate 12. A photodiode PD receives light emitted by the chips LED$_1$ and LED$_2$ for detecting a change in the amount of light from these LED chips in response to a change in ambient temperatures. The photodiode PD is provided on substrate 12 and in the vicinity of the LED chips. A hemispherical transparent molding material such as a glass epoxy or the like, which forms a first transparent layer 21, is formed on substrate 12 to cover the chips LED$_1$ and LED$_2$ and the photodiode PD. A hemispherical transparent molding material such as a glass epoxy or the like, which is a second transparent layer 22, is formed on the first transparent layer 21. At least one of the first and second transparent layers 21 and 22 is preferably formed of a material which intercepts light other than a wavelength of a spectrum emitted by the chips $LED_1$ and $LED_2$. In the first embodiment, the first transparent layer 21 employs an epoxy resin of the type which has a transparence property shown in FIG. 7 and limits a wavelengths band. Referring to FIG. 7, the curve (1) represents the transparence property of the epoxy resin for limiting the wavelength band. $\lambda_1$ designates a wavelength in a spectrum emitted by $LED_1$ and $\lambda_2$ designates a wavelength in a spectrum emitted by $LED_2$. The epoxy resin is appropriately selected from resins, for example, Toray Hysol THL-5000A/B, HL3000 (S), EX-012/HX-021-3 and the like manufactured by Toray Hysol Co., Ltd.

A very thin air layer 200 is formed at an interface between the first and second transparent layers 21 and 22 when the second transparent layer 22 is applied over the first transparent layer 21. The refractive index of this air layer is smaller than those of both the first and second transparent layers 21 and 22.

Figure 6:
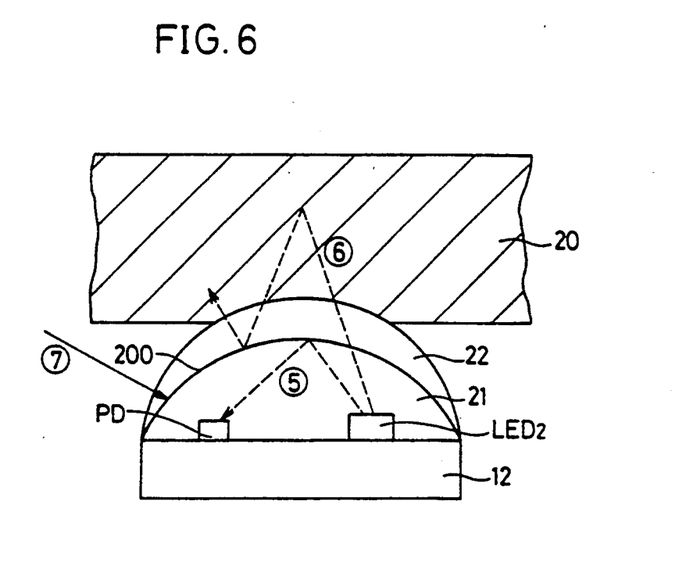
FIG. 6 is a side view for use in explaining an operation of the light emitting diode for a photosensor according to said first embodiment.

The operation will now be described, with reference to FIG. 6. The light emitting diode for a photosensor is applied to contact a living body 20. Since the air layer 200 with a small refractive index is formed at an interface 200 between the first and second transparent layers 21 and 22, a portion of light emitted by the chips $LED_1$ and $LED_2$ undergoes a total reflection at the interface 200 and then reaches the photodiode PD, as shown by the dotted line (5). Since the amount of the light subjected to the total reflection increases, the amount of the light emitted by the chips $LED_1$ and $LED_2$ and which is directly received by the photodiode PD, increases.

Light which is scattered or reflected by the living body 20 as shown by the dotted line (6), of the light emitted by the chips $LED_1$ and $LED_2$ and then entering into the living body 20, is reflected at the air layer interface 200 and hence does not reach the photodiode PD. In addition, since the first transparent layer 21 employs the epoxy resin, which has the transparence property shown in FIG. 7 which limits a wavelengths band, other light indicated by the solid line (7) with a wavelength other than the wavelength of the light emitted by the chips $LED_1$ and $LED_2$ cannot be incident on the first transparent layer 21 because the light (7) is intercepted at interface 200.

Due to the just described construction of the light emitting diode for a photosensor according to the invention of light emitted by the LED chips and directly incident on the photodiode increases, thereby making it possible to disregard the amount of light which is reflected by the living body and enters into the photodiode. This enables a precise feedback and consequently a precise measurement independently of any to influence caused by a drift of temperatures.

Although an epoxy resin is used for the first and second transparent layers 21 and 22 in the foregoing embodiment, the present invention is not limited to this material and any transparent body, for example, glass or an elastomer may be used.

While no specific explanation has been given on the thickness of the air layer, the air layer may have a thickness which arises naturally when molding the second transparent layer on the first transparent layer. In further detail, the thickness of the air layer may merely be larger than the wavelength of the light emitted by the LED chips.

Moreover, while in the example the first and second transparent layers 21 and 22 are hemispherical, the present invention is not limited to this feature. However, formation of the transparent layers 21 and 22 in a hemispherical shape has the advantage of facilitating the manufacture of these transparent layers.

Figure 8:
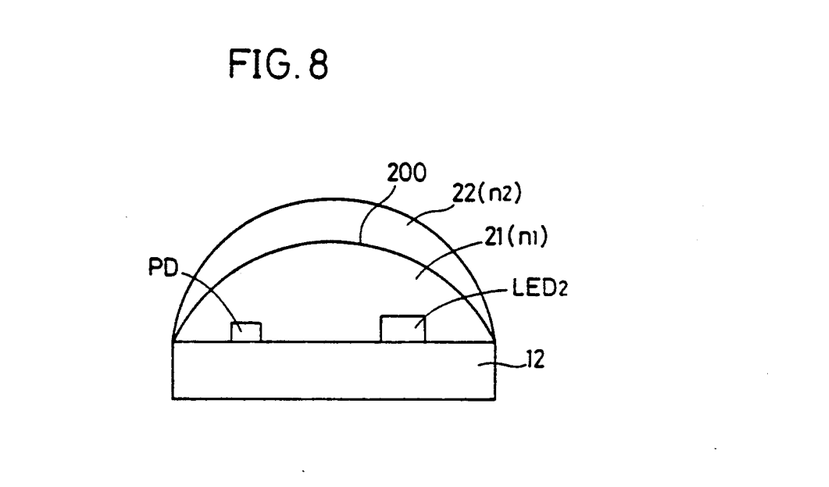
FIG. 8 is a side view of a light emitting diode for a photosensor according to a second embodiment of the present invention.

FIG. 8 is a side view of a light emitting diode for a photosensor according to another embodiment of the present invention, including a substrate 12. LED chips $LED_1$ (not shown) and $LED_2$ serving as light emitting elements are provided on substrate 12. A photodiode PD receives light emitted by the chips $LED_1$ and $LED_2$ for detecting a change in the amount of the light from the LED chips in accordance with a change in ambient temperature, is provided on the substrate 12 and near the LED chips. A hemispherical transparent molding material such as a glass epoxy or the like, which forms a first transparent layer 21, is formed on substrate 12 to cover the chips $LED_1$ and $LED_2$ and the photodiode PD. A hemispherical transparent molding material such as of a glass epoxy or the like, which forms a second transparent layer 22, is formed on the first transparent layer 21. The refractive index $n_1$ of the first transparent layer is larger than the refractive index $n_2$ of the second transparent layer. The above-described clear epoxy resin is appropriately selected from resins, for example, Toray Hysol THL-5000A/B, HL3000 (S) and EX-012/HX-021-3 manufactured by Toray Hysol Co., Ltd. The refractive indexes are adjusted by changing the compositions of the resins or by changing the mixing ratios of the resins. In the manufacturing of the present device the first transparent layer 21 which is clear epoxy, is first hardened and then the second transparent layer 22 which is also a clear epoxy, is applied and hardened.

A very thin air layer 200 in FIG. 8 is formed at an interface between the first and second transparent layers 21 and 22 in the step of forming the second transparent layer 22 on the first transparent layer 21.

The operation will now be described.

Figure 9:
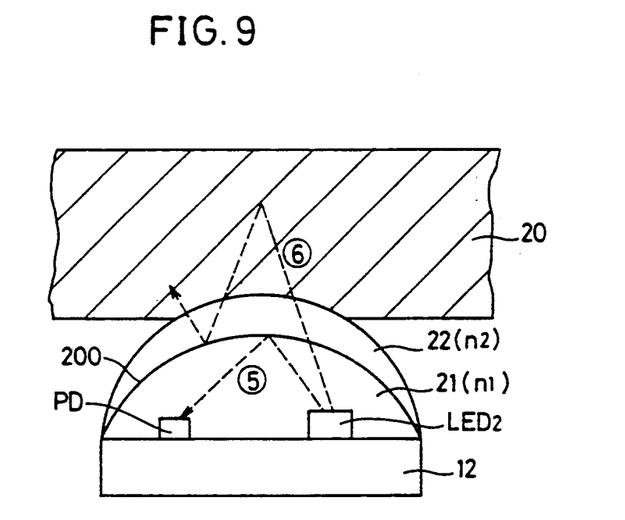
FIG. 9 is a side view for use in explaining an operation of the light emitting diode shown in FIG. 8.

Referring to FIG. 9, the light emitting diode for a photosensor is applied to contact a living body 20. Since refractive index $n_1$ of first transparent layer 21 is larger than $n_2$ of the second transparent layer 22, a portion of the light emitted by the chips $LED_1$ and $LED_2$ undergoes a total reflection at the interface and reaches the photodiode PD, as shown by the dotted line (5). In this embodiment, since the amount of the light subjected to the total reflection increases, the amount of the light emitted by the LED chips, which is directly received by the photodiode PD, also increases.

The light scattered or reflected by the living body 20 shown by the dotted line (6), of the light which is emitted by the chips $LED_1$ and $LED_2$, is then incident on the living body 20, undergoes a total reflection at the interface between the first and second transparent layers 21 and 22 and thus does not reach the photodiode PD.

By eliminating light scattering by the living body from the measurement; it becomes possible to retain a constant amount of light and obtain a precise feedback, thereby assuring a precise measurement independently of any influence caused by a drift of temperatures.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A light emitting diode for a photosensor, comprising: a substrate (12), a light emitting element provided on said substrate (12), a light receiving element disposed on said substrate (12) in the vicinity of said light emitting element for receiving light emitted by said light emitting element to detect a change in the amount of the light coming from said light emitting element in response to a change in ambient temperature, a first transparent layer (21) provided on said substrate (12) to cover said light emitting element and said light receiving element (PD), a second transparent layer (22) provided on said first transparent layer (21), and an air layer interposed between said first and said second transparent layers for substantially eliminating adverse influences of ambient temperature drifts on a measurement.

2. The light emitting diode according to claim 1, wherein
said air layer has a thickness larger than a wavelength of the light emitted by said light emitting element.

3. The light emitting diode according to claim 1, wherein
an interface between said first and second transparent layers (21, 22) is hemispherical.

4. The light emitting diode according to claim 3, wherein
a surface of said second transparent layer (22) is hemispherical.

5. The light emitting diode according to claim 1, wherein
said first transparent layer (21) is formed of a material for intercepting light other than a wavelength out of a spectrum of the light emitted by said light emitting element.

6. The light emitting diode according to claim 1, wherein said first transparent layer (21) is formed of a transparent body capable of limiting a wavelength band region.

7. The light emitting diode according to claim 6, wherein
said transparent body for limiting the wavelength band region includes an epoxy resin.

8. A light emitting diode for a photosensor, comprising:
a substrate (12);
a light emitting element provided on said substrate (12);
a light receiving element (PD) disposed on said substrate (12) and in the vicinity of said light emitting element for receiving light emitted by said light emitting element, to detect a change in the amount of the light coming from said light emitting element in accordance with a change in ambient temperature;
a first transparent layer (21) provided on said substrate (12) to cover said light emitting element and said light receiving element (PD); and
a second transparent layer (22) provided on said first transparent layer (21), wherein
a refractive index $n_1$ of said first transparent layer (21) and a refractive index $n_2$ of said second transparent layer (22) satisfy an inequality, $n_1 \geq n_2$.

* * * * *

UNITED STATES PATENT AND TRADEMARK OFFICE
CERTIFICATE OF CORRECTION

PATENT NO. : 5,151,628

DATED : September 29, 1992

INVENTOR(S) : Masahiko Osawa

It is certified that error appears in the above-identified patent and that said Letters Patent is hereby corrected as shown below:

On the title page:

[57] ABSTRACT, line 3, replace "measurment." by --measurement.--;
line 8, after "light" (first occurrence) insert --coming--;
after "light" (second occurrence) delete "coming".

Claim 1, column 7, line 1, after "element" insert --(PD)--.

Signed and Sealed this

Fourteenth Day of September, 1993

BRUCE LEHMAN

Attest:

Attesting Officer

Commissioner of Patents and Trademarks